(12) United States Patent
Leitner et al.

(10) Patent No.: US 9,162,949 B2
(45) Date of Patent: Oct. 20, 2015

(54) METHOD FOR THE PRODUCTION OF ALIPHATIC ALCOHOLS AND/OR THEIR ETHERS, IN PARTICULAR, 1-OCTANOL

(71) Applicant: Rheinisch-Westfälische Technische Hochschule (RWTH) Aachen, Aachen (DE)

(72) Inventors: Walter Leitner, Aachen (DE); Jennifer Julis, Düsseldorf (DE)

(73) Assignee: Rheinisch-Westfalische Technische Hochschule (RWTH) Aachen, Aachen (DE)

( * ) Notice: Subject to any disclaimer, the term of this patent is extended or adjusted under 35 U.S.C. 154(b) by 0 days.

(21) Appl. No.: 14/383,732

(22) PCT Filed: Mar. 28, 2013

(86) PCT No.: PCT/EP2013/056772
§ 371 (c)(1),
(2) Date: Sep. 8, 2014

(87) PCT Pub. No.: WO2013/144315
PCT Pub. Date: Oct. 3, 2013

(65) Prior Publication Data
US 2015/0141704 A1 May 21, 2015

(30) Foreign Application Priority Data
Mar. 30, 2012 (EP) ..................... 12162687

(51) Int. Cl.
*C07C 29/145* (2006.01)
*C07C 29/60* (2006.01)
*C07C 29/132* (2006.01)
*C07C 31/125* (2006.01)
*C07C 43/04* (2006.01)

(52) U.S. Cl.
CPC ............. *C07C 29/145* (2013.01); *C07C 29/132* (2013.01); *C07C 29/60* (2013.01); *C07C 31/125* (2013.01); *C07C 43/04* (2013.01)

(58) Field of Classification Search
CPC .. C07C 29/145; C07C 29/132; C07C 31/125; C07C 43/04
See application file for complete search history.

(56) References Cited

U.S. PATENT DOCUMENTS

| 2,768,978 A | 10/1956 | Robertson | |
| 2014/0228596 A1* | 8/2014 | Allgeier et al. | ................ 564/467 |

FOREIGN PATENT DOCUMENTS

| CN | 102068986 A | 5/2011 |
| GB | 682 260 | 11/1952 |
| JP | 2009-046417 A | 3/2009 |
| JP | 2010-047543 A | 3/2010 |
| WO | 2008/151178 A1 | 12/2008 |
| WO | 2011/149339 A1 | 12/2011 |

OTHER PUBLICATIONS

International Search Report for corresponding International Application No. PCT/EP2013/056772 mailed Jul. 29, 2013.
Chia et al., "Selective Hydrogenolysis of Polyols and Cyclic Ethers over Bifunctional Surface Sites on Rhodium-Rhenium Catalysts", Journal of the American Chemical Society, vol. 133, No. 32, 2011, pp. 12675-12689.
Russell et al., "Polyhydroxyalkanes from Furfural Condensation Products", Journal of the American Chemical Society, vol. 74, 1952, pp. 4543-4546.
Koso et al., "Mechanism of the hydrogenolysis of ethers over silica-supported rhodium catalyst modified with rhenium oxide", Journal of Catalysis, vol. 280, No. 2, 2011, pp. 221-229.
Koso et al., "Promoting effect of Mo on the hydrogenolysis of tetrahydrofurfuryl alcohol to 1,5-pentanediol over Rh/SiO2", Journal of Catalysis, vol. 267, No. 1, 2009, pp. 89-92.

(Continued)

*Primary Examiner* — Shailendra Kumar
(74) *Attorney, Agent, or Firm* — Renner, Otto, Boisselle & Sklar, LLP (57) ABSTRACT

A method for the production of aliphatic alcohols and/or their ethers, comprising the step of reacting a substrate of the general formula (I): in which m is 0, 1, 2, 3, 4, 5, 6, 7, 8 or 9 and n is 1 or 2; R1 is hydrogen, a linear, branched or cyclic alkyl rest, a primary alkanol rest, an aryl rest or one of the following radicals: and R2 is hydrogen or —CH₂OH; with hydrogen in the presence of a hydrogenation catalyst system, wherein the hydrogenation catalyst system comprises: a hydrogenation catalyst comprising Re, Fe, Ru, Os, Co, Rh, Ir, Ni, Pd and/or Pt; and an acidic additive selected from the group of organoperfluorocarboxylic acids, hydrochloric acid, formic acid, acetic acid, phosphoric acid, sulfuric acid, sulfonic acid and/or organic compounds comprising sulfonic acid groups, phosphoric acid groups and/or phosphonic acid groups; with the proviso that the acidic additive is a liquid and/or at least partially dissolved in the substrate (I) during the reaction of (I) with hydrogen in the case that R2 is CH₂OH.

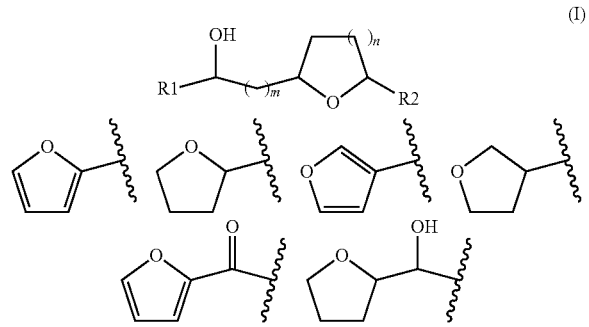

11 Claims, 2 Drawing Sheets

(56) References Cited

OTHER PUBLICATIONS

Database WPI Week 201163 Thomson Scientific, London, GB; AN 2011-H56354 XP002681779, & CN 102068986 A (Univ East China Sci&Technology) May 25, 2011.

Corma et al., "Chemical Routes for the Transformation of Biomass into Chemicals", Chemical Reviews, vol. 107, 2007, pp. 2411-2502.

Geilen et al., "Selective and Flexible Transformation of Biomass-Derived Platform Chemicals by a Multifunctional Catalytic System", Angew. Chem. Int. Ed., vol. 49, 2010, pp. 5510-5514.

Julis et al., "Selective hydrogeneration of biomass derived substrates using ionic liquid-stabilized ruthenium nanoparticles", Green Chemistry, vol. 12, 2010, pp. 1634-1639.

Huber et al., "Production of Liquid Alkanes by Aqueous-Phase Processing of Biomass-Derived Carbohydrates", Science, vol. 308, 2005, pp. 1446-1450.

Chatterjee et al., "Production of linear alkane via hydrogenative ring opening of a furfural-derived compound in supercritical carbon dioxide", Green Chemistry, vol. 12, 2010, pp. 779-782.

Winterle et al., "Katalytische Umsetzung von Cellobiose", Chemie Ingenieur Technik, vol. 82, No. 8, 2010, pp. 1211-1214.

Chatterjee et al., "An attempt to achieve the direct hydrogenolysis of tetrahydrofurfuryl alcohol in supercritical carbon dioxide", Catalysis Science & Technology, vol. 1, 2011, pp. 1466-1471.

Roman-Leshkov et al., "Production of dimethylfuran for liquid fuels from biomass-derived carbohydrates", Nature, vol. 447, 2007, pp. 982-985.

Seri et al., "Highly Efficient Catalytic Activity of Lanthanide(III) Ions for Conversion of Saccharides to 5-Hydroxymethyl-2-furfural in Organic Solvents", Chemistry Letters, 2000, pp. 22-23.

Binder et al., "Simple Chemical Transformation of Lignocellulosic Biomass into Furans for Fuels and Chemicals", Journal of the American Chemical Society, vol. 131, 2009, pp. 1979-1985.

Chheda et al., "Liquid-Phase Catalytic Processing of Biomass-Derived Oxygenated Hydrocarbons to Fuels and Chemicals", Angewandte Chemie International Edition, vol. 46, 2007, pp. 7164-7183.

Kuster, "5-Hydroxymethylfurfural (HMF). A Review Focussing on its Manufacture", Starch/Starke, vol. 41, No. 8, 1990, pp. 314-421.

* cited by examiner

FIG. 1

FIG. 2

METHOD FOR THE PRODUCTION OF ALIPHATIC ALCOHOLS AND/OR THEIR ETHERS, IN PARTICULAR, 1-OCTANOL

This application is a 371 of PCT/EP2013/056772, filed Mar. 28, 2013.

The present invention relates to the production of aliphatic alcohols and/or their ethers, wherein a tetrahydrofurane-type or tetrahydropyrane-type substrate is hydrogenated. The invention also relates to the use of a catalyst system comprising a hydrogenation catalyst and an acidic additive for hydrogenation and hydrogenolysis reactions.

As a consequence of diminishing fossil resources and the global efforts to reduce anthropogenic carbon dioxide emission, biomass-derived substrates are receiving increasing interest for a renewable supply chain to transportation fuels and chemical products. Carbohydrates present the largest fraction of biomass feedstock. Their conversion to tailor-made products can be envisaged via a set of platform molecules through selective catalytic transformation steps.

Primary alcohols of medium chain lengths are very important industrial products as they are valuable compounds for the production of detergents and surfactants, in perfumery and as flavors. 1-octanol is of particular importance and is also used for the synthesis of 1-octene, an important copolymer for polyethylene. 1-octanol is predominantly synthesized either by the reaction of ethylene with triethylaluminum (Al-fol-process) or by oxo synthesis starting with n-heptene, which are both petrochemical processes.

Biomass derived aliphatic alcohols are currently accessible only for short chains ($\leq C_4$) via fermentation or for long chains ($\geq C_{14}$) by fatty acid ester reduction, for example of coconut oil ($C_{16}$) or palm oil ($C_{18}$). A review publication covering these topics is Corma, S. Iborra, A. Velty, Chemical Reviews 2007, 107, 2411-2502. In contrast, the formation of alcohols of medium chain length from biogenic substrates has been described in only a few examples. 1-pentanol has been observed as by-product, for example, in the hydrogenolysis of tetrahydrofurfuryl alcohol and in the selective transformation of itaconic acid to 2-methyl-tetrahydrofuran.

It would be desirable to further utilize biomass derived platform molecules, such as furfural and acetone, opening a general strategy for the synthesis of medium chain length alcohols on basis of carbohydrates as feedstock.

Recently, a concept of synthetic pathway design for biomass-derived products in analogy to the retrosynthesis analysis used in modern organic synthesis has been proposed (M. A. Geilen, B. Engendahl, A. Harwardt, W. Marquardt, J. Klankermayer, W. Leitner, Angewandte Chemie 2010, 122, 5642-5646). 1-octanol can be traced back to furfural and acetone as starting materials using this approach. They are readily converted to furfuralacetone (FFA) by aldol condensation which can be hydrogenated to 4-(2-tetrahydrofuryl)-2-butanol (THFA). This could be converted into 1-octanol (1-OL) by selective deoxygenation and ring opening. Currently, however, only the hydrogenation without ring opening (J. Julis, M. Holscher, W. Leitner, Green Chemistry 2010, 12, 1634-1639) or the deep hydrogenation to alkanes is described in literature for furfuralacetone and related substrates (G. W. Huber, J. N. Chedda, C. J. Barrett, J. A. Dumesic, Science 2005, 308, 1446-1450; M. Chatterjee, K. Matsushima, Y. Ikushima, M. Sato, T. Yokoyama, H. Kawanami, T. Suzuki, Green Chem. 2010, 12, 779-782).

Therefore, the challenge to establish this pathway is the development of a catalytic system which gives selectively access to 1-octanol starting with THFA by selective deoxygenation of the secondary alcohol function coupled with the selective ring opening of the tetrahydrofuryl ring via hydrogenolysis.

Other selected publications in the field of catalytic conversion of biomass include S. Winterle and M. A. Liauw, Chemie Ingenieur Technik 2010, 82, 1211-1214 (Ru-nanoparticles in combination with acid functionalized ionic liquids convert cellobiose to sorbitol, sorbitan and isosorbid) and M. Chatterjee, H. Kawanami et al., Catalysis Science & Technology 2011, 1, 1466-1471 (an attempt to achieve the direct hydrogenolysis of tetrahydrofurfuryl alcohol in supercritical carbon dioxide).

JP 2009-046417 has the object of providing a method for the ring opening of a cyclic ether with high ring opening selectivity at a specific site thereof. In a ring opening reaction of a cyclic ether where a hydroxyalkyl group is bound to a carbon atom in its ether linkage, a Rh-bearing catalyst and metal element(s) selected from Re, Mo and W are made to coexist with the cyclic ether. In this ring opening reaction, the bond between an oxygen atom and the carbon atom to which the hydroxyalkyl group in the ether linkage is bound can be cleaved in high selectivity.

JP 2010-047543 is concerned with a method for preparing a linear alkane at high efficiency by carrying out hydrogenation and a ring-opening reaction of a furfural derivative (HMF) in a supercritical carbon dioxide fluid. The preparation method of the alkane includes steps of: carrying out aldol condensation of 5-hydroxymethylfurfural (HMF) and an acetone to obtain an aldol condensation product; and subjecting the aldol condensation product to dehydration/hydrogenation using the supercritical carbon dioxide fluid as a reaction solvent so as to synthesize a semi-hydrogenated intermediate compound or the ring-opened linear alkane.

WO 2008/151178 A1 describes a method for making a composition comprising alkanes. The composition is suitable for use as a liquid transportation fuel in general, and jet fuel in particular. The method includes dehydrating a feedstock solution comprising a carbohydrate, in the presence of an acid catalyst, to yield at least one furan derivative compound, in a reaction vessel containing a biphasic reaction medium: an aqueous reaction solution and a substantially immiscible organic extraction solution. The furan derivative compound is then subjected to a self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated or partially saturated compound, followed by hydrodeoxygenation (e.g., dehydrating and hydrogenating) of the saturated or partially saturated compound to yield a composition of matter comprising alkanes.

WO 2011/149339 A1 relates to a method for preparing caprolactone, comprising converting 5-hydroxymethyl-2-furfuraldehyde by hydrogenation into at least one intermediate compound selected from the group of 2,5-tetrahydrofuran-dimethanol, 1,6-hexanediol and 1,2,6-hexanetriol, and preparing caprolactone from said intermediate compound. Furthermore, the publication relates to a method for preparing 1,2,6-hexanetriol comprising preparing 5-hydroxymethyl-2-furfaldehyde from a renewable source, converting 5-hydroxymethyl-2-furfaldehyde into 2,5-tetrahydrofuran-dimethanol and converting 2,5-tetrahydrofuran-dimethanol into 1,2,6-hexanetriol. The publication also relates to a method for preparing 1,6-hexanediol from 1,2,6-hexanetriol, wherein 1,2,6-hexanetriol is subjected to a ring closure reaction, thereby forming (tetrahydro-2H-pyran-2-yl)methanol, and the (tetrahydro-2H-pyran-2-yl)methanol is hydrogenated, thereby forming 1,6-hexane diol.

It would be particularly desirable to gain access to the linear $C_8$-alcohol (C8-OL) which can be formed directly as free 1-octanol (1-OL) or upon reversible etherification as dioctylether (DOE). The present invention has the object of providing a method for the production of medium-chain alcohols which can be derived from renewable sources.

According to the present invention this object has been achieved by a method for the production of aliphatic alcohols and/or their ethers, comprising the step of reacting a substrate of the general formula (I):

(I)

in which m is 0, 1, 2, 3, 4, 5, 6, 7, 8 or 9 and n is 1 or 2;
R1 is hydrogen, a linear, branched or cyclic alkyl rest, a primary alkanol rest, an aryl rest or one of the following radicals:

and R2 is hydrogen or —$CH_2OH$;
with hydrogen in the presence of a hydrogenation catalyst system, wherein the hydrogenation catalyst system comprises:
  a hydrogenation catalyst comprising Re, Fe, Ru, Os, Co, Rh, Ir, Ni, Pd and/or Pt; and
  an acidic additive selected from the group of organoperfluorocarboxylic acids, hydrochloric acid, formic acid, acetic acid, phosphoric acid, sulfuric acid, sulfonic acid and/or organic compounds comprising sulfonic acid groups, phosphoric acid groups and/or phosphonic acid groups;
  with the proviso that the acidic additive is a liquid and/or at least partially dissolved in the substrate (I) during the reaction of (I) with hydrogen in the case that R2 is $CH_2OH$.

It has surprisingly been found that the catalyst system according to the invention provides for a hydrogenolysis of the cyclic ether without unduly deoxygenating the substrate to the alkane. In particular, n-alkanols or their ethers may be obtained by selective deoxygenation of one OH group in the molecule while a second OH group remains intact.

Examples for hydrogenation catalysts include heterogenous catalysts comprising one or more of the above-mentioned metals. Furthermore, homogenous catalysts based on these metals may be used.

The hydrogen employed may be molecular hydrogen sourced as $H_2$. Another possibility is to employ hydride compounds or a transfer hydrogenation reaction. For example, one may use hydrogen donor reagents including (but not limited to) formic acid and/or isopropanol. A transfer hydrogenation with formic acid derived from biomass is specifically envisaged.

Organic compounds comprising the above-mentioned acid groups specifically include ionic liquids in which the anion and/or the cation comprises these acid groups (acidic ionic liquids).

The method according to the invention may be carried out in neat substrate without additional solvent or in solution using organic solvents, ionic liquids or supercritical fluids. An example for an organic solvent is hexane or heptane.

With respect to the acidic additive, in the case that R2 is hydrogen no limitations are made concerning a solid, liquid, gaseous or dissolved state of the additive in the reaction mixture. If R2 is $CH_2OH$, the acidic additive is a liquid under reaction conditions (this includes biphasic liquid/liquid systems) and/or is at least partially dissolved in the substrate under reaction conditions. This may also be the case for a gaseous acidic additive. If a solvent is used, then the acidic additive is to be at least partially dissolved in the liquid phase comprising at least the solvent.

For both alternatives of R2 it is possible to use an acidic ionic liquid additive as described above as a liquid layer on a solid support. This is known as a supported ionic liquid phase (SILP) or solid catalyst with ionic liquid layer (SCILL).

The acidic additive may be present in amounts of ≥0.01 weight-% to ≤25 weight-%, preferably ≥0.1 weight-% to ≤5 weight-%, with respect to the substrate (I).

Concerning reaction conditions, suitable reaction temperatures may be, for example, in a range of ≥50° C. to ≤300° C., preferably ≥100° C. to ≤200° C. The hydrogen gas pressure may be in a range of ≥1 bar to ≤300 bar, preferably ≥50 bar to ≤200 bar, more preferred ≥120 bar to ≤180 bar.

In the context of this invention, the expression "alkyl" includes acyclic saturated or unsaturated hydrocarbon radicals, which can be branched- or straight-chain and unsubstituted or mono- or polysubstituted, having 1 to 20 C atoms. Methyl, ethyl, n-propyl and iso-propyl, n-butyl, sec-butyl and iso-butyl are particularly preferred.

For the purpose of this invention, the expression "cyclic alkyl" denotes cyclic hydrocarbons having 3, 4, 5, 6, 7 or 8 carbon atoms, wherein the hydrocarbons can be saturated or unsaturated (but not aromatic), unsubstituted or mono- or polysubstituted. It is advantageously chosen from the group which contains cyclopropyl, cyclobutyl, cyclopentyl, cyclohexyl, cycloheptyl, cyclooctyl, cyclopentenyl, cyclohexenyl, cycloheptenyl and cyclooctenyl.

A "primary alkanol rest" is a rest of the type —$(CH_2)_o$—OH in which o is from 1 to 20. Examples include —$C_2H_4$—OH and $C_3H_6$—OH.

In the context of this invention, the expression "aryl" denotes aromatic hydrocarbons having up to 14 ring members, inter alis phenyls and naphthyls. The aryl radicals can also be condensed with further saturated, (partially) unsaturated or aromatic ring systems. Each aryl radical can be unsubstituted or mono- or polysubstituted, wherein the substituents on the aryl can be identical or different and can be in any desired and possible position of the aryl. Aryl is advantageously chosen from the group which contains phenyl, 1-naphthyl, 2-naphthyl, which can in each case be unsubstituted or mono- or polysubstituted.

The present invention will be described in greater detail in connection with specific embodiments. They may be combined freely unless the context clearly indicates otherwise. Throughout the text, the term "IL" is to be understood as "ionic liquid". Unless specified otherwise, ionic liquids are defined as ionic compounds with melting points below 100° C.

In one embodiment of the method according to the invention the reaction is carried out in the presence of a non-acidic ionic liquid as a solvent. The term "non-acidic" is especially to be understood as "non-Brönstedt-acidic", i.e. not comprising any proton-donating functional groups. Examples for suitable non-acidic ionic liquids include non-acidic phosphonium ionic liquids and compounds of the general formulas (III) to (VI):

in which each of R10, R11, R12 are independently of each other H, methyl, ethyl, propyl, butyl, pentyl, hexyl or a heavier alkyl or aryl group; and each of R12, R13, R14, R15 and R16 are independently of each other methyl, ethyl, propyl, butyl, pentyl, hexyl or a heavier alkyl or aryl group. Furthermore, the anion $X^-$ may be halogenide, $HSO_4^-$, OTf (Tf=$SO_2CF_3$), $NTf_2$, tetrafluoroborate, hexafluorophosphate and/or trifluoroacetate. A particularly preferred non-acidic ionic liquid is 1-ethyl-3-methylimidazolium bis(trifluoromethylsulfonyl)imide, commonly known as [EMIM][$NTf_2$] or [EMIM][BTA].

The use of a non-acidic ionic liquid as a solvent allows to fine-tune the reactivity of the acidic additive to achieve the desired reaction profile without unwanted further reactions. If acidic ionic liquids are used as the acidic additive, it is particularly preferred to use a non-acidic analogon as the solvent. An example of this is the combination of [EMIM][$NTf_2$] and [$BSO_3BIM$][$NTf_2$] (1-(4-butylsulfonic acid)-3-(n-butyl)-imidazolium bis(trifluoromethylsulfonyl)imide).

In another embodiment of the method according to the invention the hydrogenation catalyst is Ru nanoparticles stabilized by an ionic liquid; Ru; Ru/C; Ru/alumina; and/or Ru/silica. With respect to Ru/C, Ru/alumina and Ru/silica, the metal catalyst loading may be in the range of ≥1 weight-% to ≤10 weight-%, preferably ≥4 weight-% to ≤6 weight-%.

As used herein, the term "nanoparticles" means particles of a solid or semisolid material having a weight average diameter, as determinable by scanning electron microscopy (SEM) or transmission electron microscopy (TEM) in the range of 1-1000 nm, in particular in the range of 5-500 nm.

Metal nanoparticles are thermodynamically unstable and must be stabilized in solution to prevent agglomeration. Stabilization can be achieved by steric and/or electronic shielding and ILs have been shown to combine both modes of action. ILs often bind less strongly to the metal surface than other stabilizing agents, resulting in nanoparticles with high catalytic activity. IL-stabilized transition metal nanoparticles can be easily generated by controlled decomposition of organometallic compounds or the reduction of transition metal compounds. The ruthenium nanoparticles can be synthesized by reduction of bis(methylallyl)(1,5-cyclooctadiene) ruthenium(II) suspended in the IL at a metal loading of, for example, 2.5 weight-% at 60° C. and 60 bar hydrogen pressure.

As imidazolium based ILs have proven to be suitable for the stabilization of nanoparticles, imidazolium based ILs differing in the nature of the anion, the chain length or the substituent at the C2-position can used. It is possible to vary the alkyl chain length to modulate the polarity and the substituents at C2-position to change the coordination ability. A set of anions differing in their nucleophilicity and coordination strength can be chosen, as these factors are expected to influence the stability of nanoparticles.

Suitable ionic liquids for the stabilization include [EMIM][$NTf_2$], [EMIM][Acetate], [EMIM][Br], [BMIM][$BF_4$] (1-butyl-3-methylimidazolium tetrafluoroborate) and/or [$C_{12}MIM$][$NTf_2$] (1-dodecyl-3-methylimidazolium bis(trifluoromethylsulfonyl)imide).

In another embodiment of the method according to the invention the acidic additive is toluenesulfonic acid and/or an imidazolium compound comprising an alkylsulfonic acid group bound to the imidazolium ring. Particularly preferred imidazolium compounds are those of the formula (VII):

wherein y is 0, 1, 2, 3 or 4 and z=0, 1, 2, 3 or 4 and $X^-$ is $HSO_4^-$, OTf (Tf=$SO_2CF_3$) or $NTf_2$. Most preferred is [$BSO_3BIM$][$NTf_2$] (1-(4-butylsulfonic acid)-3-(n-butyl)-imidazolium bis(trifluoromethylsulfonyl)imide).

In another embodiment of the method according to the invention in the substrate (I) m is 2, n is 1 and R1 is methyl. These substrates may be obtained by the aldol condensation of acetone with furfural or 5-hydroxymethylfurfural and subsequent hydrogenation of the double bonds in the molecule:

Furfural and 5-hydroxymethylfurfural can be obtained from renewable sources. The term "renewable source" is used herein in particular for materials that can be naturally replenished from living organisms. Fossil materials that have been transformed by geological processes, such as coal, oil or the like, are not renewable sources. More in particular, renewable sources include biomass which may be obtained from living material (e.g. plant matter, or components isolated there from such as lignocellulose, cellulose, starch, or glucose). A preferred source of biomass is agricultural waste (agro waste), which is formed by parts of agricultural crops that are not used for animal or human consumption. Normally it would be composted, largely to $CO_2$.

In another embodiment of the method according to the invention the hydrogenation is performed at a temperature of ≥120° C. to ≤180° C. Preferably the temperature is ≥140° C. to ≤160° C. It is also preferred that the hydrogen pressure during the reaction is ≥120 bar to ≤150 bar, in particular ≥110 bar to ≤130 bar. Furthermore, a preferred weight ratio of catalyst to substrate (I) is ≥1:1000 to ≤1:500, in particular ≥1:150 to ≤1:50, based on the weight of the catalytically active metal and the substrate.

A further aspect of the present invention is a method for the production of aliphatic alcohols and/or their ethers, comprising the steps of:

A) reacting a substrate of the general formula (II):

(II)

in which R1 is hydrogen, a linear, branched or cyclic alkyl rest, a primary alkanol rest, an aryl rest or one of the following radicals:

and R2 is hydrogen or —CH$_2$OH;

with hydrogen in the presence of a hydrogenation catalyst comprising Re, Fe, Ru, Os, Co, Rh, Ir, Ni, Pd and/or Pt and in the absence of an acidic additive as described in step B); thereby obtaining a first mixture which also comprises the hydrogenation catalyst;

B) adding an acidic additive selected from the group of organoperfluorocarboxylic acids, hydrochloric acid, formic acid, acetic acid, phosphoric acid, sulfuric acid, sulfonic acid and/or organic compounds comprising sulfonic acid groups, phosphoric acid groups and/or phosphoric acid groups to the first mixture obtained in step A); thereby obtaining a second mixture;

C) contacting the second mixture obtained in step B) with hydrogen;

with the proviso that the acidic additive is a liquid and/or at least partially dissolved in the second mixture during step C) in the case that R2 is CH$_2$OH.

In the interest of avoiding repetition, reference is made to the definitions for the substituents, etc. as already outlined above. This aspect of the invention will also be described together with specific embodiments which may be combined freely unless the context clearly indicates otherwise.

In one embodiment of this method steps A), B) and C) are performed consecutively in the same reaction vessel. Therefore, a "one-pot" procedure is achieved.

In another embodiment of this method steps A), B) and/or C) are performed in one or more flow reactors. The reactor(s) may be of the plug-flow type or of the (continuously) stirred-tank type. Furthermore, catalysts may be in a fixed catalyst bed. A preferred weight ratio of catalyst to substrate (I) is ≥1:1000 to ≤1:500, in particular ≥1:150 to ≤1:50, based on the weight of the catalytically active metal and the substrate.

Therefore, the first and the second hydrogenation step may be directly coupled in the sense that the hydrogenations are carried out in the same reactor, or in the sense that the product of the first hydrogenation reaction is continuously fed from a first reactor into a second reactor or from a first reaction zone inside a reactor (wherein the first hydrogenation reaction is carried out) into a second reaction zone inside that reactor (wherein the second hydrogenation step is carried out).

In particular, the product of the first hydrogenation reaction may be directly fed from the first reactor or first reaction zone into the second reactor or first reaction zone. As used herein, 'directly fed' in particular means fed without intermediate storage of the product, without intermediate chemical reaction steps, and without intermediate purification steps.

In another embodiment of this method the substrate (II) is obtained by the base-catalyzed condensation of ketone (III) and furane (IV):

in which R1 is hydrogen, a linear, branched or cyclic alkyl rest, a primary alkanol rest, an aryl rest or one of the following radicals:

and R2 is hydrogen or —CH$_2$OH;

followed by neutralization and conducting of steps A), B) and C) in the same reaction vessel in which the base-catalyzed condensation of (III) and (IV) was conducted.

Furane (IV) is furfural or 5-hydroxymethyl furfural (HMF). The HMF may in principle be obtained in any way, in particular from any renewable source. Preferably, the HMF has been prepared from a carbohydrate. The carbohydrate may in particular be selected from the group of fructose, glucose, sucrose, starch, cellulose and lignocellulose, including mixtures of any two or more of these, e.g. a mixture comprising glucose and fructose.

HMF can be prepared from fructose by an acid-catalyzed dehydration reaction. This may be accomplished in a manner known per se, for instance in aqueous/organic mixtures, catalyzed by sulphuric acid as described by Dumesic and coworkers (Nature 2007, 447, 982-985) or in DMSO catalyzed by LaC (Ishida and coworkers, Chemistry Letters 2000, 22-23). Another method is described in Joseph B. Binder, and Ronald T. Raines, J. Am. Chem. Soc, 2009, 131 (5), 1979-1985. Further, several reviews exist that describe the various processes, such as: Dumesic and co-workers, Angewandte Chemie International Edition, 2007 46 7164-7183 and B. F. M. Kusters, Starch, 1990, 8, 314-321. The contents of these publications regarding the reaction conditions of preparing HMF are incorporated by reference. If a carbohydrate polymer is used, this may first be depolymerized to provide monosaccharide units (e.g. glucose or fructose). This may be accomplished in a manner known per se.

If glucose is used to prepare HMF, the glucose may first be converted into fructose, e.g. in a manner known per se. For instance, in a suitable process a product comprising glucose, such as corn syrup or another starch product, is first liquefied using an alpha-amylase, then the liquified product is enzymatically converted into glucose using a glucoamylase, and thereafter the product treated with glucoamylase is treated with glucose isomerase to give a mixture of fructose and glucose. This mixture can be separated, e.g. by simulated moving bed (SMB) to give what is called High Fructose Cornstarch Syrup (HFCS90), in case the starting product is corn syrup. This typically contains about 90 wt. % of fructose, based on dry weight. Of course, other syrups providing fructose may be used. HFCS90 is a preferred raw material for the production of HMF.

Likewise, furfural may be prepared from renewable sources. When heated with sulfuric acid, hemicellulose undergoes hydrolysis to yield sugars, principally xylose. Under the same conditions of heat and acid, xylose and other five carbon sugars undergo dehydration to yield furfural.

In another embodiment of this method steps A), B) and/or C) are carried out in the presence of a non-acidic ionic liquid as a solvent. Full reference is made to the non-acidic ionic liquids as described above. A particularly preferred non-acidic ionic liquid is 1-ethyl-3-methylimidazolium bis(trifluoromethylsulfonyl)imide, commonly known as [EMIM][NTf$_2$] or [EMIM][BTA].

In another embodiment of this method the hydrogenation catalyst in step A) and/or C) is Ru nanoparticles stabilized by an ionic liquid; Ru; Ru/C; Ru/alumina; and/or Ru/silica. Full reference is made to the hydrogenation catalysts as described above. With respect to Ru/C, Ru/alumina and Ru/silica, the metal catalyst loading may be in the range of ≥1 weight-% to ≤10 weight-%, preferably ≥4 weight-% to ≤6 weight-%. Suitable ionic liquids for the stabilization include [EMIM][NTf$_2$], [EMIM][Acetate], [EMIM][Br], [BMIM][BF$_4$] (1-butyl-3-methylimidazolium tetrafluoroborate) and/or [C$_{12}$MIM][NTf$_2$] (1-dodecyl-3-methylimidazolium bis(trifluoromethylsulfonyl)imide).

In another embodiment of this method the acidic additive in step B) is toluenesulfonic acid and/or an imidazolium compound comprising an alkylsulfonic acid group bound to the imidazolium ring. Particularly preferred imidazolium compounds are those of the formula (VII):

(VII)

wherein y is 0, 1, 2, 3 or 4 and z=0, 1, 2, 3 or 4 and X$^-$ is OTf (Tf=—SO$_2$CF$_3$) or NTf$_2$. Most preferred is [BSO$_3$BIM][NTf$_2$] (1-(4-butylsulfonic acid)-3-(n-butyl)-imidazolium bis(trifluoromethylsulfonyl)imide).

In another embodiment of this method in the substrates (II), (III) and (IV) R1 is methyl.

The present invention is also directed towards the use of a mixture comprising:
- a hydrogenation catalyst comprising Re, Fe, Ru, Os, Co, Rh, Ir, Ni, Pd and/or Pt; and
- an acidic additive selected from the group of organoperfluorocarboxylic acids, hydrochloric acid, formic acid, acetic acid, phosphoric acid, sulfuric acid, sulfonic acid and/or organic compounds comprising sulfonic acid groups, phosphoric acid groups and/or phosphonic acid groups;

as a hydrogenation catalyst system for the hydrogenation of a substrate of general formula (I):

(I)

in which m is 0, 1, 2, 3, 4, 5, 6, 7, 8 or 9 and n is 1 or 2;
R1 is hydrogen, a linear, branched or cyclic alkyl rest, a primary alkanol rest, an aryl rest or one of the following radicals:

and R2 is hydrogen or —CH$_2$OH;
with the proviso that the acidic additive is a liquid and/or at least partially dissolved in the substrate (I) during the reaction of (I) with hydrogen in the case that R2 is CH$_2$OH.

In the interest of avoiding repetition, reference is made to the definitions for the substituents, etc. as already outlined above.

The present invention will be further described with reference to the following examples without wishing to be limited by them.

GLOSSARY

THFA: 4-(2-tetrahydrofuryl)-2-butanol
FFA: furfuralacetone
[NTf$_2$]: bis(trifluoromethylsulfonyl)imide
[BCO$_2$BIM]: 1-(4-butycarboxylic acid)-3-(n-butyl)-imidazolium
[BSO$_3$BIM]: 1-(4-butylsulfonic acid)-3-(n-butyl)-imidazolium
[BSO$_3$N$_{444}$]: N,N,N-tributyl-1-(4-butylsulfonic acid)-aminium
Ru@IL: Ru nanoparticles stabilized by an ionic liquid All reactions were carried out in a. 10 mL stainless-steel high pressure reactor with a glass inlet. Metal catalysts and ionic liquids were handled under an inert atmosphere of argon. Ru@IL were prepared freshly before use by suspending [(cod)Ru(methyallyl)2] (5.0 mg, 0.016 mmol) in the corresponding ionic liquid (62 mg), followed by hydrogenation at 60° C. and 60 bar H$_2$ for two hours. Ru/C (5 wt.-%) was activated with hydrogen at 80° C. and 100 bar pressure for 10 hours prior to use. In a typical hydrogenolysis reaction 4-(2-tetrahydrofuryl)-2-butanol (THFA, 225.7 mg, 1.57 mmol), 1-ethyl-3-methylimidazolium bis(trifluoromethylsulfonyl) imide (2.9 mL) and the acidic additive (0.11 mmol) were added to the metal catalyst and the reaction mixture was stirred for 15 h at 150° C. and 120 bar $H_2$ pressure. After carefully venting the reactor, the reaction mixture was extracted with pentane (3×20 mL). The colorless solution was concentrated under reduced pressure and the composition of the products was analyzed via GC.

In a first set of experiments the transformation of THFA under hydrogen was investigated with ruthenium nanoparticles stabilized in various ionic liquids (Ru@IL; particle size 2-3 nm), which were prepared by hydrogenation of [(cod)Ru[$\eta^3$-$C_4H_7$)$_2$] according to a previously published procedure (J. Julis, M. Holscher, W. Leitner, Green Chemistry 2010, 12, 1634-1639).

TABLE 1

Hydrogenolysis of THFA with Ru @ acidic IL

| No. | Ionic liquid | Conv. | BTHF [%] | 1-OL [%] | DOE [%] | others [%] |
|---|---|---|---|---|---|---|
| 1[a] | [$BCO_2BIM$][$NTf_2$] | 0 | — | — | — | — |
| 2[a] | [$BSO_3BIM$][$NTf_2$] | >99 | 5.0 | — | — | 95 |
| 3[b] | [$BSO_3BIM$][$NTf_2$] | >99 | 66.6 | 25 | 2.8 | 5.6 |
| 4[b] | [$BSO_3BIM$][OTf] | >99 | 69.0 | 9.7 | 1.0 | 21.2 |
| 5[b] | [$BSO_3N_{444}$][$NTf_2$] | >99 | 75.3 | 3.2 | 0 | 21.5 |

[a]120° C., 120 bar $H_2$, 15 h, Ru/Substrate 1:100, 2.5 wt.-% Ru in acidic IL
[b]120° C., 120 bar $H_2$, 15 h, Ru/Substrate 1:100, c(S) = 0.5 mol/L, 2.5 wt.-% Ru in acidic IL, EMIM $NTf_2$; others: isomers and etherification products of THFA.

As seen from Table 1, the Ru@[$BCO_2BIM$][$NTf_2$] catalyst showed no activity in the hydrogenolysis of THFA, indicating that the acidity of the carbonic acid function in the ionic liquid is too weak for the dehydration. In contrast the performance of Ru@ [$BSO_3BIM$][$NTf_2$] was dominated by the acidic function, resulting mainly in etherification and isomerization of THFA. The use of Ru@[$BSO_3BIM$][OTf] and Ru@[$BSO_3N$][$NTf_2$] resulted in a combination of hydrogenation and acid catalysis leading to BTHF in up to 75% yield, but large amounts of isomerization and etherification products of THFA were still present. Finally, it was possible to reduce the acid catalyzed side-reactions by diluting the catalyst Ru@[$BSO_3BIM$][$NTf_2$] with [EMIM][$NTf_2$] as inert IL, and the formation of 1-OL and DOE became significant with 28% yield for C8-ol (overall yield of 1-OL+DOE) and high selectivity towards 1-OL. Therefore, this system was chosen as first lead structure for further investigation.

Figure 1:
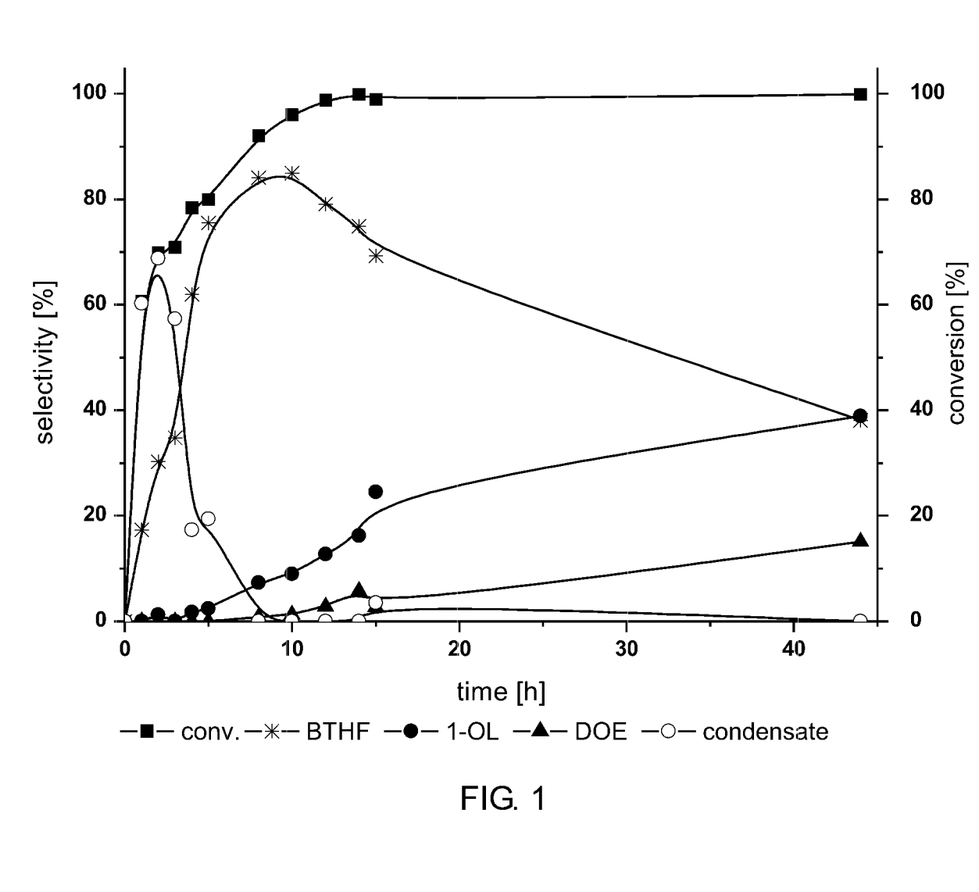

Monitoring the reaction (Ru@[$BSO_3BIM$][$NTf_2$] catalyst; FIG. 1) reveals that acid catalyzed self-etherification and isomerization of the substrate also occur with this system and dominate the product formation during the first two hours. The hydrogenolysis of the secondary alcohol group in the side chain of THFA, however, reverses the etherification equilibrium and the deoxygenation product BTHF is accumulated with a maximum of 80% in the reaction mixture after eight hours reaction time. Selective reductive ring opening of the tetrahydrofuryl ring in BTHF gives access to 1-OL, which again undergoes subsequent partial etherification to DOE under of the acidic conditions. Further dehydration to n-octane remains insignificant under these conditions reflecting that the primary alcohol function is much more resistant to acid catalyzed hydrogenolysis than secondary alcohols.

The monitoring of the reaction reveals that the hydrogenolysis of THFA is a network of consecutive reaction involving uni- and bimolecular transformations of the substrate and product, respectively. Therefore, the reaction parameters temperature, reaction time and substrate concentration were selected for further optimization using a simplex algorithm with the yield of 1-OL as target value. The parameter limits were set to T=120° C. to 160° C., t=10 h to 25 h and $c^0$(THFA)=0.2 mol/L to 0.8 mol/L, while hydrogen pressure and the substrate to catalyst ratio were kept constant.

After 16 iteration steps the alteration of the command variable reached a stable output within the tolerance of errors. The optimized reaction condition are 150° C., 15 h and 0.5 mol/L substrate concentration with a maximum yield of 45% 1-OL and an overall C8-ol yield of 71.4%. The two octanol-based products DOE and 1-OL were formed almost exclusively under the optimized reaction conditions within this simplex algorithm optimization.

Using the optimized conditions, a series of combinations of Ru-based catalysts and acidic additives was evaluated (Table 2, entries 1 to 7). Ru@[$N_{444}BSO_3$] showed a slightly higher combined yield for the C8-OL products with a lower 1-OL/DOE-ratio and small amounts of n-octane as compared to the imidazolium ionic liquid (entry 1 and 2). Commercially available Ru/C and Ru/Alox catalysts also gave good to excellent yields for C8-OL, albeit results varied significantly with the source of the catalysts.

The data presented in Table 2 were obtained with Ru/C (5%) obtained from ABCR and Strem were found to be reproducible within +/−4.5% between 3 independent experiments and with two different batches of catalyst.

TABLE 2

Catalyst screening at optimized reaction conditions.

| No. | substrate | Catalyst | Additive | BTHF [%] | 1-OL [%] | DOE [%] | octane [%] | others [%] | Yield $C_8$-ol [%] |
|---|---|---|---|---|---|---|---|---|---|
| 1 | THFA[a] | Ru @ [$BSO_3BIM$][$NTf_2$] | — | 25.8 | 44.9 | 26.1 | — | 3.2 | 71.4 |
| 2 | THFA[a] | Ru @ [$BSO_3N_{444}$][$NTf_2$] | — | 11.7 | 41.5 | 34.5 | 2.4 | 9.9 | 76.7 |
| 3 | THFA[a] | Ru/C (5 wt.-% Ru) | [$BSO_3BIM$][$NTf_2$] | 58.6 | 27.1 | 9.1 | — | 5.1 | 36.5 |
| 4 | THFA[a] | Ru/C (5 wt.-% Ru) | p-TsOH | 8.7 | 24.7 | 51.9 | 8.5 | 6.2 | 76.9 |
| 5 | THFA[a] | Ru/Alox (5 wt.-% Ru) | [$BSO_3BIM$][$NTf_2$] | 23.0 | 43.6 | 31.8 | — | 1.6 | 75.9 |
| 6 | FFA[c] | Ru @ [$C_{12}MIM$][$NTf_2$] | [$BSO_3BIM$][$NTf_2$] | 4.5 | — | — | — | 95.5* | 0 |
| 7 | FFA[c] | Ru/C | [$BSO_3BIM$][$NTf_2$] | 5.4 | 48.4 | 44.2 | — | 1.8 | 93.1 |
| 8 | FFA[c] | Ru/C | p-TsOH | 2.1 | 18.1 | 53.0 | 16.9 | 10.8 | 71.1 |
| 9 | Furfural[d] | Ru/C | [$BSO_3BIM$][$NTf_2$] | 23.5 | 32.5 | 19.8 | — | 24.2* | 54.1 | conversion ≥99 %, 2.5 wt.-% Ru in acidic additive
[a]150° C., 120 bar $H_2$, 15 h, c(S) = 0.5 mol/L, Ru/Substrate 1:100;
[b]same conditions as [a], 30 h;
[c]1. 120° C., 120 bar $H_2$, 2 h, Ru/substrate 1:100, 2. 150° C., 120 bar $H_2$, 45 h, acidic additive, EMIM $NTf_2$;
[d]1. FF/Acetone 1:10, rt, 15 h, 50 µL 1.0M NaOH, 2. 120° C., 120 bar $H_2$, 2 h, Ru/substrate 1:100, 2. 150° C., 120 bar $H_2$, 60 h, EMIM $NTf_2$;
others: mainly 2-propyltetrahydro-pyran,
*isomers of THFA In combination with p-toluenesulfonic acid (p-TsOH), an overall yield to C8-OL of 77% was achieved within 15 h, whereby the larger content of DOE and the formation of significant amounts of n-octane reflect the higher acidity (entry 4). In comparison Ru/C together with [BSO$_3$BIM][NTf$_2$] was slightly less active but gave outstanding selectivities for the deoxygenation of the secondary OH function (entries 5-7).

Once the transformation of THFA to C8-OL had been successfully demonstrated, further integration was attempted. If the reaction sequence is performed in individual steps with intermediate isolation of the products, more than 95% yield can be achieved in each step corresponding to an overall yield of 73% based on furfural. Control experiments showed that furfuralacetone (FFA) is very sensitive towards acidic conditions and forms humin-type products in the presence of p-TsOH and [BSO$_3$BIM][NTf$_2$]. This excludes a direct one step conversion of FFA to C8-Ol using the multifunctional catalyst systems. However, a two-step one-pot process can successfully be achieved when the acidic additive is introduced directly into the reaction vessel after full hydrogenation of FFA to THFA (Table 2, entries 7 and 8).

After FFA was hydrogenated at 120° C. and 120 bar H$_2$ for two hours in presence of Ru/C, the acidic IL [BSO$_3$BIM] [NTf$_2$] and the solvent [EMIM][NTf$_2$] were added and the reaction mixture was treated further at 150° C. and 120 bar H$_2$ for 60 hours to obtain 1-OL and DOE in excellent combined yields of 86%. Some n-octane was formed with p-TsOH as acidic additive, whereas the ruthenium nanoparticles were completely inactive for the hydrogenation in the second step due to agglomeration and deactivation during the sequence.

Figure 2:
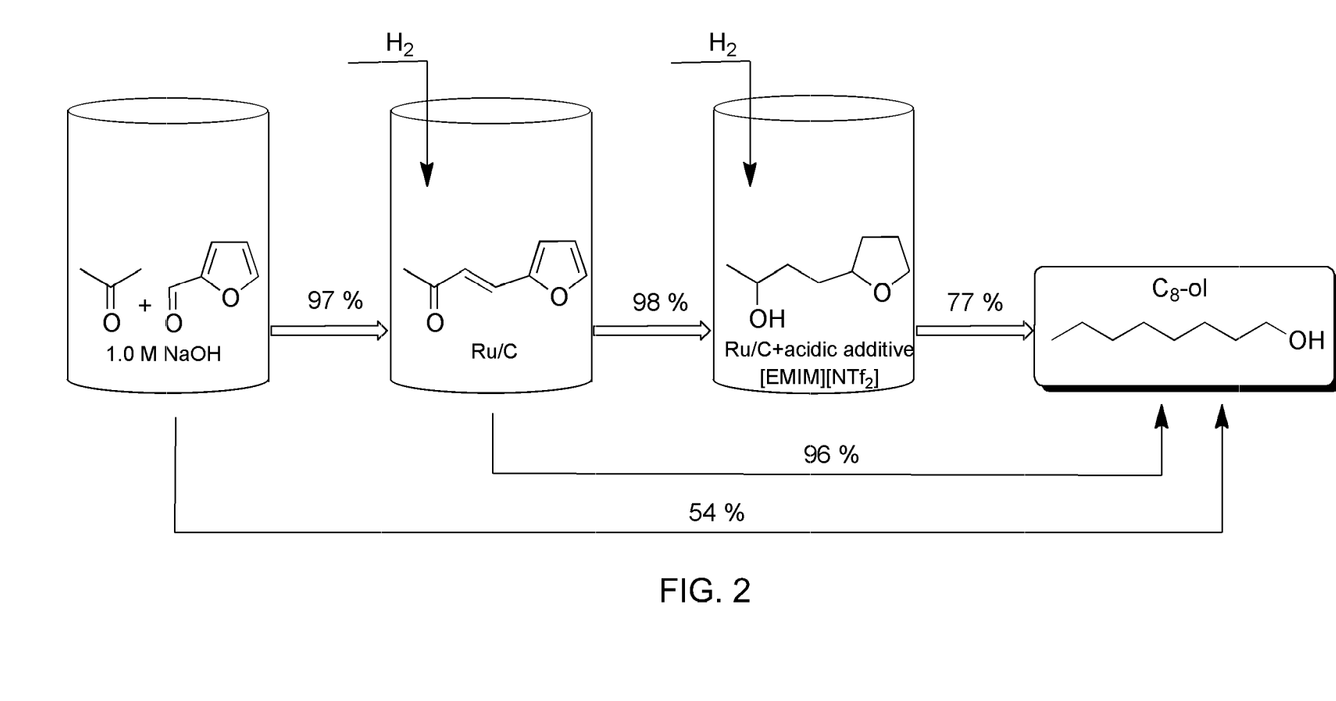

Finally, it was demonstrated that it is even possible to conduct this reaction sequence as one-pot procedure starting from furfural as a platform chemical (FIG. 2). Furfural was transformed to FFA via aldol condensation in the presence of excess acetone using sodium hydroxide under standard conditions. After neutralization of the reaction mixture with aqueous HCl and evaporation of acetone, Ru/C was added and the hydrogenation carried out as above.

After 2 h, the acidic IL [BSO$_3$BIM][NTf$_2$] and the solvent IL were introduced directly for the final step. The overall yield for C8-OL was 54% with a higher content of 1-OL corresponding to a remarkable 33% yield of the free alcohol. The somewhat lower overall yield can be attributed at least partly to the presence of the salt resulting from the neutralization process.

The invention claimed is:

1. A method for the hydrogenolysis of cyclic ethers, comprising the step of reacting a substrate of the general formula (I):

in which m is 2, 3, 4, 5, 6, 7, 8 or 9 and n is 1 or 2;

R1 is hydrogen, a linear, branched or cyclic alkyl rest, a primary alkanol rest, an aryl rest or one of the following radicals:

and R2 is hydrogen or —CH$_2$OH;

with hydrogen in the presence of a hydrogenation catalyst system, wherein the hydrogenation catalyst system comprises:

a hydrogenation catalyst comprising Ru; and an acidic additive selected from the group of acidic ionic liquids comprising sulfonic acid groups, phosphoric acid groups and/or phosphonic acid groups;

with the proviso that the acidic additive is a liquid and/or at least partially dissolved in the substrate (I) during the reaction of (I) with hydrogen in the case that R2 is CH$_2$OH;

and wherein ruthenium nanoparticles stabilized by 1-ethyl-3-methylimidazolium bis(trifluoromethylsulfonyl) imide, 1-ethyl-3-methylimidazolium bis (trifluoromethylsulfonyl) acetate, 1-ethyl-3-methylimidazolium bis(trifluoromethylsulfonyl) bromide, (1-butyl-3-methylimidazolium tetrafluoroborate and/or (1-dodecyl-3-methylimidazolium bis(trifluoromethylsulfonyl) imide) are excluded as a catalyst;

and wherein the hydrogenation is performed at a temperature of ≥140° C. to ≤180° C.

2. The method according to claim 1, wherein the reaction is carried out in the presence of a non-acidic ionic liquid as a solvent.

3. The method according to claim 1, wherein the acidic additive is an imidazolium compound comprising an alkylsulfonic acid group bound to the imidazolium ring.

4. The method according to claim 1, wherein in the substrate (I) m is 2, n is 1 and R1 is methyl.

5. A method for hydrogenating a substrate of the general formula (II), comprising the steps of:

A) reacting a substrate of the general formula (II):

in which R1 is hydrogen, a linear, branched or cyclic alkyl rest, a primary alkanol rest, an aryl rest or one of the following radicals:

and R2 is hydrogen or —CH$_2$OH;
with hydrogen in the presence of a hydrogenation catalyst comprising Ru and in the absence of an acidic additive as described in step B); thereby obtaining a first mixture which also comprises the hydrogenation catalyst;

B) adding an acidic additive selected from the group of acidic ionic liquids comprising sulfonic acid groups, phosphoric acid groups and/or phosphonic acid groups to the first mixture obtained in step A); thereby obtaining a second mixture;

C) contacting the second mixture obtained in step B) with hydrogen;
  with the proviso that the acidic additive is a liquid and/or at least partially dissolved in the second mixture during step C) in the case that R2 is CH$_2$OH;
  and wherein ruthenium nanoparticles stabilized by 1-ethyl-3-methylimidazolium bis(trifluoromethylsulfonyl) imide, 1-ethyl-3-methylimidazolium bis(trifluoromethylsulfonyl) acetate, 1-ethyl-3-methylimidazolium bis(trifluoromethylsulfonyl) bromide, (1-butyl-3-methylimidazolium tetrafluoroborate and/or (1-dodecyl-3-methylimidazolium bis(trifluoromethylsulfonyl) imide) are excluded in step C.

6. The method according to claim 5, wherein steps A), B) and C) are performed consecutively in the same reaction vessel.

7. The method according to claim 5, wherein steps A), B) and/or C) are performed in one or more flow reactors.

8. The method according to claim 5, wherein the substrate (II) is obtained by the base-catalyzed condensation of ketone (III) and furane (IV):

(III)

(IV)

in which R1 is hydrogen, a linear, branched or cyclic alkyl rest, an aryl rest or one of the following radicals:

and R2 is hydrogen or —CH$_2$OH;
followed by neutralization and conducting of steps A), B) and C) in the same reaction vessel in which the base-catalyzed condensation of (III) and (IV) was conducted.

9. The method according to claim 5, wherein steps A), B) and/or C) are carried out in the presence of a non-acidic ionic liquid as a solvent.

10. The method according to claim 1, wherein the acidic additive in step B) is an imidazolium compound comprising an alkylsulfonic acid group bound to the imidazolium ring.

11. The method according to claim 5, wherein in the substrates (II), (III) and (IV) R1 is methyl.

* * * * *